United States Patent [19]

Tanaka et al.

[11] 4,396,764

[45] Aug. 2, 1983

[54] CYANOGUANIDINE DERIVATIVES

[75] Inventors: Satoru Tanaka, Higashikurume; Katsutoshi Shimada, Tokyo; Kazunori Hashimoto, Matsudo; Kiichi Ema; Koichiro Ueda, both of Tokyo, all of Japan

[73] Assignee: Eisai Co., Ltd., Tokyo, Japan

[21] Appl. No.: 302,360

[22] Filed: Sep. 15, 1981

Related U.S. Application Data

[62] Division of Ser. No. 178,017, Aug. 13, 1980, Pat. No. 4,327,217, which is a division of Ser. No. 120,876, Feb. 12, 1980, Pat. No. 4,287,346.

[30] Foreign Application Priority Data

Feb. 16, 1979 [JP]  Japan .................................. 54-15989
Feb. 16, 1979 [JP]  Japan .................................. 54-15990

[51] Int. Cl.³ .................. C07D 213/57; C07D 213/38; C07D 401/12
[52] U.S. Cl. .................................... 544/124; 546/194; 546/264; 546/330; 546/281
[58] Field of Search ............... 546/281, 194, 264, 330; 544/124

[56] References Cited

U.S. PATENT DOCUMENTS 4,327,217  4/1982  Tanaka et al. ...................... 546/281

Primary Examiner—John M. Ford
Attorney, Agent, or Firm—Wenderoth, Lind & Ponack

[57] ABSTRACT

Novel cyanoguanidine derivatives, and acid addition salts thereof useful as medicines which have pharmacological actions such as anti-secretory effect, local anesthesia action and the like; and process for the preparation thereof.

13 Claims, No Drawings

CYANOGUANIDINE DERIVATIVES

This application is a divisional application of application Ser. No. 178,017, filed Aug. 13, 1980 (now U.S. Pat. No. 4,327,217), which application is in turn a divisional application of application Ser. No. 120,876, filed Feb. 12, 1980 (now U.S. Pat. No. 4,287,346).

This invention relates to novel cyanoguanidine derivatives, acid addition salts thereof having excellent actions as medicines and to the process for the preparation thereof, wherein the cyanoguanidine derivatives are represented by the general formula:

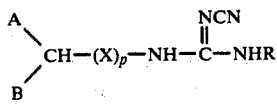

(I)

wherein

A represents a substituted or unsubstituted phenyl, furyl, thienyl or cycloalkyl group;

B represents pyridyl, phenyl, or pyridine-N-oxide group;

R represents a lower alkyl group, a lower alkenyl group, or a group of the formula:

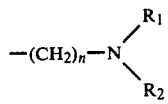

wherein $R_1$ and $R_2$ are the same or different, and each represent a lower alkyl group, or together form nitrogen-containing heterocycle with the nitrogen atom to which they bond, and n is an integer of 1-3, or R represents a group of the formula:

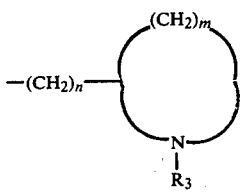

wherein $R_3$ is a lower alkyl group, n is an integer of 1-3 and m is an integer of 4-5;

X represents an alkylene or an alkylene group containing the terminal sulfur atom; and p is 0 or 1, with the proviso that (i) when A is unsubstituted phenyl and B is pyridyl, p is 1 and R is a group of the formula:

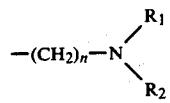

or a group of the formula:

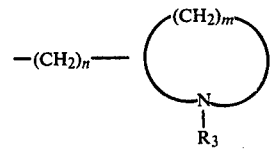

and (ii) when A is unsubstituted phenyl and B is phenyl or pyridine-N-oxide, p is 0; and intermediate therefor represented by the general formula:

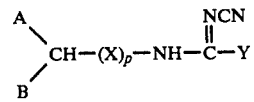

(V)

wherein Y represents a lower alkoxy or a lower alkylthio group, and A, B, X and p have the same meanings as defined above.

Illustrative substituents on the substituted phenyl groups mentioned for the definition of A in the general formula (I) include, practically, a lower alkyl, lower alkenyl, halogen, lower alkoxy, lower alkylthio, lower alkylsulfonyl, halogen substituted lower alkyl groups and the like. The term "lower" used in the above illustration is meant for any straight or branched carbon chains containing 1-6 carbon atoms. Illustrative said lower alkyl groups may include, for example, methyl, ethyl, n-propyl, isopropyl, isobutyl, 1-methylpropyl, tert-butyl, n-pentyl, 1-ethylpropyl, isoamyl, n-hexyl and the like, and lower alkenyl groups may include isopropenyl, allyl, crotyl, methallyl and the like.

The lower alkoxy or a lower alkylthio group mentioned for the definition of Y in the general formula (V) has also 1-6 carbon atoms.

The term "halogen" means practically fluoro, chloro, iodo or bromo group.

The cycloalkyl group means practically a cycloalkyl group containing 5-6 carbon atoms. The lower alkyl and lower alkenyl groups shown in the definitions of R, $R_1$ and $R_2$ have the same meanings as those defined above.

Further, illustrative nitrogen-containing heterocycles formed by the groups $R_1$ and $R_2$, with nitrogen atom to which they bond, include, for example, pyrrolidine, piperidine, piperazine, morpholine and the like.

Alkylene represented by X means lower alkylene groups, such, for example, as methylene, ethylene, propylene, and the like, which may contain a terminal sulfur atom. The pyridyl group represented by B may be combined at any one of the 2, 3 and 4 positions on the pyridine ring.

There are some tautomers of the compound (I) of this invention, and these tautomers are, of course, included in this invention.

The compound (I) of this invention may be easily converted into the pharmacologically acceptable acid addition salt by reacting it with an inorganic or organic acid. Illustrative inorganic acids include hydrochloric, hydrobromic, hydroiodic, sulfuric acids and the like, and illustrative organic acids include maleic, fumaric, succinic, acetic, malonic, citric, benzoic acids and the like.

The compounds to be provided according to this invention are all novel compounds which have not as yet been reported in the literature. Said compounds have very excellent and broad pharmacological actions as medicine, such as, very intensively, gastric juice secretion inhibitory or antisecretory, antidepressant, local anesthesia, antidiarrheal, antiedema, diuretic, hypertensive, hypotensive, vasoconstrictive, antiserotonin, smooth muscle relaxing, coronary vasodilative, and bradycardia actions and the like. Thus, the compounds (I) of this invention are useful as various medicines due to such pharmacological actions. Illustrative medicines include antipeptic ulcer drug, antidepressant, local anesthetics, anti-inflammatory agents, diuretics, antiallergic agents, antidiarrheal, hypertensive, hypotensive, antiarrhythmic agent, muscle relaxants, coronary vasodilator and the like.

Since the inhibitory action of the compounds according to this invention to gastric juice secretion is not based on the anticholine action, the compound of this invention do not exhibit the side effect due to the anticholine action. This is a great characteristic of the compounds according to this invention, and therefore the compounds are particularly expected as a new type antipeptic ulcer drug among the various medicines mentioned above.

The compounds (I) of this invention can be prepared through various processes. Among these processes, the following shows one process which may be usually employed.

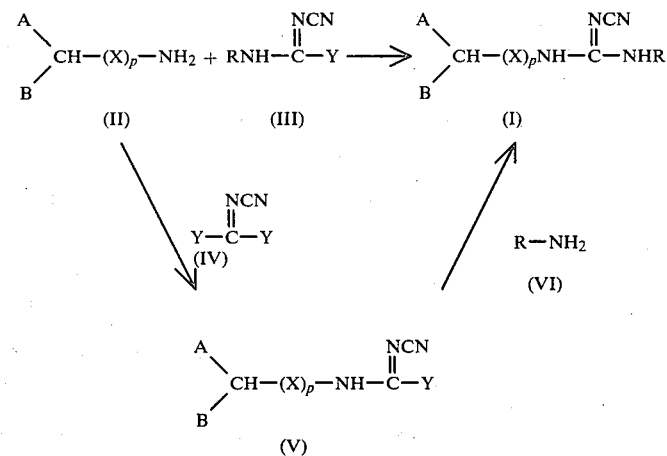

wherein Y represnts a lower alkoxy or a lower alkylthio group, and A, B, R, X and p have the same meanings as defined above.

Process (1) for the Preparation

The compounds (I) of this invention are produced, in one step, by reacting the amine derivative represented by the above formula (II) with an isothiourea derivative or an isourea derivative represented by the above formula (III). This reaction may be effected in the presence or absence of solvent.

An excess amount of the amine derivative may be used as a solvent. However, it is desirable to use, for example, methanol, ethanol, isopropanol, acetonitrile, chloroform and the like as solvent. The reaction is effected at room temperature or elevated temperature. The reaction may be effected under reflux, when solvent is used.

Process (2) for the Preparation

The compounds represented by the general formula (I) of this invention are produced, through two steps, by reacting the amine derivative represented by the general formula (II) with a compound represented by the general formula (IV) to produce a compound represented by the general formula (V), followed by reacting the latter compound (V) with an amine represented by the general formula (VI). According to this process, both reactions of said two steps may be effected with the similar procedures as the reaction between the amine derivative (II) and the isothiourea derivative or isourea derivative (III) as described above. This reaction may be also effected without separating the compound (V) from the reaction vessel after the reaction of the amine derivative (II) with the compound (IV).

The excellent pharmacological actions of the compounds of this invention are illustrated hereinafter with respect to typical compounds of this invention.

1. Anti-secretory effect

Inhibitory ratio to the gastric juice serection was determined by the Shay rat 4 hr method [H. Shay et al.; Gastroentrogy, vol. 5, P. 43 (1945)]. Results are shown in Table 1.

TABLE 1

| | Compound | Oral dosage (mg/Kg) | Inhibitory ratio (%) |
|---|---|---|---|
| Known compound | Cimetidine (control) | 50 | 85.8 |
| Compound of this invention | N—cyano-N'—methyl-N—[α-(2-pyridyl)benzyl]guanidine (control) | 100 | 69.3 |
| | N—cyano-N'—ethyl-N—[α-(2-pyridyl)ortho-methylbenzyl]guanidine | 50 | 93.5 |
| | N—cyano-N'—allyl-N—[α-(2-pyridyl)ortho-methylbenzyl]guanidine | 50 | 79.0 |
| | N—cyano-N'—methyl-N—[α-(2-pyridyl)ortho-methoxybenzyl]guanidine | 50 | 91.6 |
| | N—cyano-N'—ethyl-N—[α-(2-pyridyl)ortho-methoxybenzyl]guanidine | 50 | 96.7 |
| | N—cyano-N'—ethyl-N—[α-(2-pyridyl)metha-chlorobenzyl]guanidine | 50 | 79.2 |
| | N—cyano-N'—(3-diethylaminopropyl)-N—[α-(2- | | |

TABLE 1-continued

| Compound | Oral dosage (mg/Kg) | Inhibitory ratio (%) |
|---|---|---|
| pyridyl)benzyl]guanidine | 100 | 81.0 |
| N—cyano-N'—(1-ethyl pyrrolyl-2)-methyl-N—[α-(2-pyridyl)benzyl]guanidine | 100 | 86.0 |

2. Anti-depressant efficacy

Anti-depressant efficacy was determined using mouse by the method as described in G. Chen and B. Bohner: J. Pharmac. Exptl. Therap. 131, 179 (1961).
Results are shown in Table 2.

TABLE 2

| | Compound | Minimum effective dose (mouse, oral dosage mg/Kg) |
|---|---|---|
| Known compound | Imipramine (control) | 10 |
| | N—cyano-N'—methyl-N—[α-(2-pyridyl)benzyl/guanidine (control) | 25 |
| Compound of this invention | N—cyano-N'—ethyl-N—[α-(2-pyridyl)ortho-methylbenzyl]guanidine | 1 |
| | N—cyano-N'—methyl-N—[α-(2-pyridyl)metha-methylbenzyl]guanidine | 10 |
| | N—cyano-N'—ethyl-N—[α-(2-pyridyl)ortho-methoxybenzyl]guanidine | 10 |
| | N—cyano-N'—ethyl-N—[α-(2-pyridyl)ortho-chlorobenzyl]guanidine | 10 |
| | N—cyano-N'—methyl-N—[α-(2-pyridyl)metha-chlorobenzyl]guanidine | 2.5 |

3. Local anesthesia action

Local anesthesia action was determined by the method as described in M. R. A. Chance et al., J. Pharmac. Exptl. Therap. 82, 203 (1944). Results are shown in Table 3.

TABLE 3

| | Compound | Minimum effective concentration (%) |
|---|---|---|
| Known compound | Dibucaine (control) | 0.1 |
| | N—cyano-N'—methyl-N—[α-(2-pyridyl)benzyl]guanidine (control) | >3 |
| Compound of this invention | N—cyano-N'—(1-ethyl-pyrolidyl-2)methyl-N—[α-(2-pyridyl)para-methylbenzyl]guanidine | 0.5 |
| | N—cyano-N'—(3-dimethyl-aminopropyl)-N—[α-(2-pyridyl)paramethylbenzyl]guandine | 0.5 |
| | N—cyano-N'—(1-ethylpyro-lidyl-2)methyl-N—[α-(2-pyridyl)orthomethoxy-benzyl]guanidine | 0.25 |

4. Antidiarrheal action

TABLE 4

| | Compound | Minimum effective dose (mouse, oral dosage, mg/Kg) |
|---|---|---|
| Known compound | Atropine (control) | 60 |
| | N—cyano-N'—methyl-N—[α-(2-pyridyl)benzyl]guanidine (control) | 50 |
| Compound of this invention | N—cyano-N'—ethyl-N—[α-(2-pyridyl)ortho-methylbenzyl]guanidine | 1 |
| | N—cyano-N'—allyl-N—[α-(2-pyridyl)ortho-methylbenzyl]guanidine | 10 |
| | N—cyano-N'—ethyl-N—[α-(2-pyridyl)ortho-chlorobenzyl]guanidine | 5 |
| | N—cyano-N'—methyl-N—[α-(2-pyridyl)metha-chlorobenzyl]guanidine | 10 |
| | N—cyano-N'—methyl-N—[α-(2-pyridyl)metha-trifluoromethylbenzyl]guanidine | 25 |

5. Antiedema action

Antiedema action was determined using rat by the method as described C. A. Winter, et al.: Proc. Soc. Exp. Biol. Med. 111, 544 (1962). Results are shown in Table 5.

TABLE 5

| | Compound | Minimum effective dose (rat, oral dosage, mg/Kg) |
|---|---|---|
| Known compound | Indomethacin (control) | |
| | N—cyano-N'—methyl-N—[α-(2-pyridyl)benzyl]guanidine (control) | >100 |
| Compound of this invention | N—cyano-N'—methyl-N—[α-(2-pyridyl)ortho-methylbenzyl]guanidine | 2.5 |
| | N—cyano-N'—ethyl-N—[α-(2-pyridyl)ortho-methylbenzyl]guanidine | 2.5 |
| | N—cyano-N'—ethyl-N—[α-(2-pyridyl)ortho-methoxybenzyl]guanidine | 2.5 |

6. Diuretics action

Diuretics action was determined by the method as described in E. Cornish: J. Pharm. Pharmacol. 18, 65 (1966). Results are shown in Table 6.

TABLE 6

| | Compound | Minimum effective dose (oral dosage mg/Kg) |
|---|---|---|
| Known compound | Hydrofulumethiazide (control) | 2.0 |
| | N—cyano-N'—methyl-N—[α-(2-pyridyl)benzyl]guanidine (control) | 5.0 |
| Compound of this invention | N—cyano-N'—ethyl-N—[α-(2-pyridyl)ortho-methylbenzyl] | |

TABLE 6-continued

| Compound | Minimum effective dose (oral dosage mg/Kg) |
|---|---|
| guanidine N—cyano-N'—ethyl-N—[α-(2-pyridyl)metha-methylbenzyl] | 0.1 |
| guanidine N—cyano-N'—ethyl-N—[α-(2-pyridyl)metha-chlorobenzyl] | 0.25 |
| guanidine N—cyano-N'—methyl-N—[α(2-pyridyl)metha-trifluoromethylbenzyl] | 0.5 |
| guanidine N—cyano-N'—allyl-N—[α-(2-pyridyl)ortho-methoxybenzyl] | 0.5 |
| guanidine | 1.0 |

As apparently seen from the results of the above pharmacological experiments, the guanidine derivatives provided according to this invention exhibit very intense pharmacological actions, as compared with the known compounds.

This invention will be more particularly illustrated by the following examples. However, it should be understood that this invention is not limited to only those examples.

EXAMPLE 1

N-cyano-N'-methyl-N-[α-(2-pyridyl)-o-methylbenzyl]-guanidine (1) (a) Dimethylcyanodithioimido carbonate in amount of 11.4 g (0.1 mol) and α-(2-pyridyl)-o-methyl-benzylamine in amount of 18.4 g (0.1 mol) were dissolved in 300 ml of ethanol. The whole was allowed to react at room temperature overnight. Crystals deposited were separated by filtration. The filtrate was concentrated to deposit an additional amount of crystals. These crystals were combined and recrystallized from ethyl acetate to produce 17.7 g (yield: 66.4%) of N-cyano-S-methyl-N-[α-(2-pyridyl)orthomethylbenzyl]isothiourea.

Melting point: 162°-4° C.

Elementary analysis of the compound having the presumed formula $C_{16}H_{16}N_4S$ gave:

| | C | H | N |
|---|---|---|---|
| Calculated (%): | 64.83 | 5.44 | 18.90 |
| Found (%): | 65.03 | 5.31 | 18.79 |

(b) A mixture consisting of 5.9 g (0.02 mol) of N-cyano-S-methyl-N-[α-(2-pyridyl)orthomethylbenzyl]isothiourea prepared in (a), 30 ml of 20% solution of methylamine in ethanol and 70 ml of ethanol was prepared and reacted at room temperature overnight. The reaction solution was concentrated under a reduced pressure. The residue was recrystallized from ethyl acetate to produce 4.7 g of the subject material, N-cyano-N'-methyl-N-[α-(2-pyridyl)orthomethylbenzyl]-guanidine (yield: 85.0%).

Melting point: 187°-9° C.

Elementary analysis of the compound having the presumed formula $C_{16}H_{17}N_5$ gave:

| | C | H | N |
|---|---|---|---|
| Calculated (%): | 68.78 | 6.13 | 25.07 |
| Found (%): | 68.83 | 6.01 | 25.26 |

(2) Alpha-(2-pyridyl)orthomethylbenzylamine in amount of 1.8 g (0.01 mol) and N-cyano-S,N'-dimethylisothiourea in amount of 1.3 g (0.01 mol) were dissolved in 50 ml of acetonitrile. The whole was reacted under heating for 10-15 hours. The reaction solution was then concentrated under reduced pressure. The residue was recrystallized from ethyl acetate to produce 1.6 g of the subject material, N-cyano-N'-methyl-N-[α-(2-pyridyl)orthomethylbenzyl]guanidine (yield: 59.0%).

Melting point: 187°-9° C.

Elementary analysis of the compound having the presumed formula $C_{16}H_{17}N_5$ gave:

| | C | H | N |
|---|---|---|---|
| Calculated (%): | 68.78 | 6.13 | 25.07 |
| Found (%): | 68.81 | 6.05 | 25.20 |

EXAMPLES 2-107

Examples 2-107 were achieved according to the process for the preparation as described in Example 1 (1) via isothiourea derivatives. Tables 7 and 8 show respectively melting point, yield (%) and elementary analysis of the resulting isothiourea derivatives and the compounds of this invention.

In Table 7, the general formula:

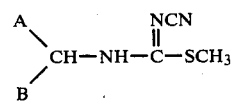

represents the formula wherein p is 0 and Y is methylthio group in the formula (V) hereinbefore mentioned.

In Table 8, the general formula:

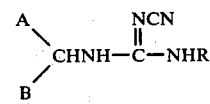

represents the formula wherein p is 0 in the formula (I).

TABLE 7

$$\begin{array}{c} A \\ \phantom{A}\diagdown \\ \phantom{AA}CH-NH-\underset{\underset{\displaystyle B}{\phantom{|}}}{\overset{\overset{\displaystyle NCN}{\|}}{C}}-SCH_3 \\ \phantom{A}\diagup \\ B \end{array}$$

| Ex. | A | B | Melting Point (°C.) | Yield | Molecular Formula | Elementary Analysis Upper line: Calcd. Lower line: Found | | |
|---|---|---|---|---|---|---|---|---|
| | | | | | | C | H | N |
| 2 | 2-CH₃-C₆H₄ | 2-pyridyl | 166–168 | 63.5 | $C_{16}H_{16}N_4S$ | 64.83 64.87 | 5.44 5.26 | 18.90 19.01 |
| 3 | 4-CH₃-C₆H₄ | 2-pyridyl | 148–149 | 76.7 | $C_{16}H_{16}N_4S$ | 64.83 65.05 | 5.44 5.36 | 18.90 18.91 |
| 4 | 2-Cl-C₆H₄ | 2-pyridyl | 119–120 | 71.7 | $C_{15}H_{13}N_4SCl$ | 56.87 56.60 | 4.10 4.09 | 17.69 17.05 |
| 5 | 3-Cl-C₆H₄ | 2-pyridyl | 205–206 | 80.1 | $C_{15}H_{13}N_4SCl$ | 56.87 56.65 | 4.10 3.94 | 17.69 17.45 |
| 6 | 4-Cl-C₆H₄ | 2-pyridyl | 121–122 | 85.5 | $C_{15}H_{13}N_4SCl$ | 56.87 56.79 | 4.10 4.06 | 17.69 17.50 |
| 7 | 2,3-Cl₂-C₆H₃ | 2-pyridyl | 118–119 | 55.3 | $C_{15}H_{12}N_4SCl_2$ | 51.28 51.09 | 3.42 3.29 | 15.95 15.62 |
| 8 | 2-OCH₃-C₆H₄ | 2-pyridyl | 126–128 | 64.5 | $C_{16}H_{16}N_4OS$ | 61.53 61.43 | 5.16 4.98 | 17.94 17.47 |
| 9 | 3-OCH₃-C₆H₄ | 2-pyridyl | 162–163 | 84.0 | $C_{16}H_{16}N_4OS$ | 61.53 61.90 | 5.16 5.03 | 17.94 17.79 |
| 10 | 4-CH₃O-C₆H₄ | 2-pyridyl | 151–152 | 70.0 | $C_{16}H_{16}N_4OS$ | 61.53 61.60 | 5.16 5.05 | 17.94 18.08 |
| 11 | 2-OCH₃,4-CH₃O-C₆H₃ | 2-pyridyl | 155–156 | 88.0 | $C_{17}H_{18}N_4O_2S$ | 59.64 59.76 | 5.30 5.24 | 16.37 16.77 |
| 12 | 2-OC₂H₅-C₆H₄ | 2-pyridyl | 117–118 | 86.5 | $C_{17}H_{18}N_4OS$ | 62.56 63.05 | 5.56 5.42 | 17.17 17.23 |
| 13 | 2-iso-OC₃H₇-C₆H₄ | 2-pyridyl | 138–139 | 87.5 | $C_{18}H_{20}N_4OS$ | 63.51 63.54 | 5.92 5.84 | 16.46 15.96 |
| 14 | 4-CH₃S-C₆H₄ | 2-pyridyl | 103–104 | 68.8 | $C_{16}H_{16}N_4S_2$ | 58.53 58.71 | 4.91 4.69 | 17.07 17.41 |
| 15 | 4-CH₃SO₂-C₆H₄ | 2-pyridyl | 139–140 | 71.1 | $C_{16}H_{16}N_4O_2S_2$ | 53.33 53.14 | 4.48 4.19 | 15.55 15.43 |
| 16 | 3-CF₃-C₆H₄ | 2-pyridyl | 163–164 | 68.1 | $C_{16}H_{13}N_4F_3S$ | 54.86 54.88 | 3.74 3.76 | 16.00 16.12 |

TABLE 7-continued $$\underset{B}{\overset{A}{>}}CH-NH-\overset{NCN}{\underset{\parallel}{C}}-SCH_3$$

| Ex. | A | B | Melting Point (°C.) | Yield | Molecular Formula | Elementary Analysis Upper line: Calcd. Lower line: Found | | |
|---|---|---|---|---|---|---|---|---|
| | | | | | | C | H | N |
| 17 |  | 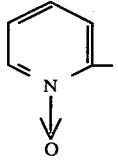 | 182–183 | 65.5 | $C_{15}H_{14}N_4OS$ | 60.40<br>60.73 | 4.70<br>4.58 | 18.79<br>18.82 |
| 18 | 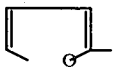 | 2-pyridyl | 116–118 | 70.0 | $C_{13}H_{12}N_4OS$ | 57.33<br>57.50 | 4.44<br>4.18 | 20.57<br>20.54 |
| 19 | 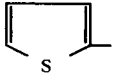 | 2-pyridyl | 104–106 | 56.0 | $C_{13}H_{12}N_4S_2$ | 54.13<br>54.43 | 4.19<br>4.18 | 19.43<br>19.72 |
| 20 |  | 2-pyridyl | 140–143 | 73.3 | $C_{15}H_{20}N_4S$ | 62.46<br>62.82 | 6.98<br>6.99 | 19.43<br>19.20 |
| 21 |  |  | 150–152 | 46.3 | $C_{16}H_{15}N_3S$ | 68.29<br>68.30 | 5.38<br>5.52 | 14.94<br>14.87 |
| 22 | 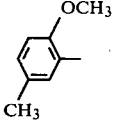 | 2-pyridyl | 152–153 | 60.1 | $C_{17}H_{18}N_4OS$ | 62.56<br>62.90 | 5.56<br>5.57 | 17.17<br>17.11 |

TABLE 8

$$\underset{B}{\overset{A}{>}}CHNH-\overset{NCN}{\underset{\parallel}{C}}-NHR$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 2 |  | 2-pyridyl | $-C_2H_5$ | 132–133 | 81.0 | $C_{17}H_{19}N_5$ | 69.59<br>69.98 | 6.52<br>6.53 | 23.87<br>23.76 |
| 3 |  | 2-pyridyl | $-CH_2CH=CH_2$ | 147–149 | 79.5 | $C_{18}H_{19}N_5$ | 70.79<br>71.21 | 6.27<br>6.16 | 22.93<br>22.96 |
| 4 |  | 2-pyridyl | $-(CH_2)_3N{\overset{C_2H_5}{\underset{C_2H_5}{<}}}$ | 115–117 | 86.0 | $C_{22}H_{30}N_6$ | 69.80<br>70.12 | 7.99<br>8.09 | 22.20<br>22.30 |
| 5 |  | 2-pyridyl | $-CH_2-\text{(N-ethylpyrrolidinyl)}$ | 171–172 | 55.5 | $C_{22}H_{28}N_6$ | 70.17<br>70.58 | 7.49<br>7.56 | 22.32<br>22.54 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 6 | CH₃-phenyl (3-methylphenyl) | 2-pyridyl | —CH₃ | 172–174 | 76.0 | C₁₆H₁₇N₅ | 68.78 / 69.09 | 6.13 / 6.14 | 25.07 / 25.07 |
| 7 | 3-methylphenyl | 2-pyridyl | —C₂H₅ | 145–147 | 83.1 | C₁₇H₁₉N₅ | 69.59 / 69.46 | 6.52 / 6.63 | 23.87 / 23.68 |
| 8 | 3-methylphenyl | 2-pyridyl | —CH₂CH=CH₂ | 112–114 | 75.5 | C₁₈H₁₉N₅ | 70.79 / 70.78 | 6.27 / 6.38 | 22.93 / 22.81 |
| 9 | 3-methylphenyl | 2-pyridyl | —CH₂-(1-ethylpyrrolidin-2-yl) | 100–102 | 47.4 | C₂₂H₂₈N₆ | 70.19 / 70.38 | 7.49 / 7.67 | 22.32 / 22.43 |
| 10 | 4-methylphenyl | 2-pyridyl | —CH₃ | 171–172 | 95.9 | C₁₆H₁₇N₅ | 68.78 / 68.97 | 6.13 / 6.30 | 25.07 / 24.95 |
| 11 | 4-methylphenyl | 2-pyridyl | —C₂H₅ | 153–154 | 87.5 | C₁₇H₁₉N₅ | 69.59 / 69.81 | 6.52 / 6.50 | 23.87 / 23.85 |
| 12 | 4-methylphenyl | 2-pyridyl | —CH₂CH=CH₂ | 144–145 | 88.0 | C₁₈H₁₉N₅ | 70.79 / 70.83 | 6.27 / 6.44 | 22.93 / 22.83 |
| 13 | 4-methylphenyl | 2-pyridyl | —(CH₂)₃—N(C₂H₅)₂ | 84–85 | 67.7 | C₂₂H₃₀N₆ | 69.80 / 69.78 | 7.99 / 8.06 | 22.20 / 22.09 |
| 14 | 4-methylphenyl | 2-pyridyl | —CH₂-(1-ethylpyrrolidin-2-yl) | 113–115 | 87.4 | C₂₂H₂₈N₆ | 70.17 / 69.94 | 7.49 / 7.54 | 22.32 / 22.29 |
| 15 | 2-chlorophenyl | 2-pyridyl | —CH₃ | 210–211 | 89.3 | C₁₅H₁₄N₅Cl | 60.10 / 60.15 | 4.67 / 4.56 | 23.40 / 23.34 |
| 16 | 2-chlorophenyl | 2-pyridyl | —C₂H₅ | 176–177 | 84.9 | C₁₆H₁₆N₅Cl | 61.24 / 61.28 | 5.10 / 4.89 | 22.33 / 22.43 |
| 17 | 2-chlorophenyl | 2-pyridyl | —CH₂CH=CH₂ | 144–145 | 81.7 | C₁₇H₁₆N₅Cl | 62.27 / 62.54 | 4.92 / 4.72 | 21.51 / 21.74 |
| 18 | 2-chlorophenyl | 2-pyridyl | —(CH₂)₃—N(C₂H₅)₂ | 103–104 | 90.1 | C₂₁H₂₇N₆Cl | 63.24 / 63.16 | 6.77 / 6.88 | 21.08 / 21.01 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|-----|---|---|---|---|---|---|---|---|---|
| | | | | | | | C | H | N |
| 19 | 2-Cl-phenyl | 2-pyridyl | $-CH_2-\underset{\underset{C_2H_5}{\|}}{\overset{}{N}}\text{(pyrrolidinyl)}$ | 169–172.5 | 70.3 | $C_{21}H_{25}N_6Cl$ | 63.56 63.56 | 6.30 6.20 | 21.18 21.24 |
| 20 | 3-Cl-phenyl | 2-pyridyl | $-CH_3$ | 194–195 | 84.2 | $C_{15}H_{14}N_5Cl$ | 60.10 60.05 | 4.67 4.62 | 23.40 23.40 |
| 21 | 3-Cl-phenyl | 2-pyridyl | $-C_2H_5$ | 153–155 | 92.9 | $C_{16}H_{16}N_5Cl$ | 61.24 61.11 | 5.10 5.14 | 22.33 22.25 |
| 22 | 3-Cl-phenyl | 2-pyridyl | $-CH_2CH=CH_2$ | 136–137 | 87.5 | $C_{17}H_{16}N_5Cl$ | 62.27 61.90 | 4.92 4.80 | 21.51 20.87 |
| 23 | 3-Cl-phenyl | 2-pyridyl | $-(CH_2)_3N(C_2H_5)_2$ | 80–84 | 69.8 | $C_{21}H_{27}N_6Cl$ | 63.24 63.30 | 6.77 6.79 | 21.08 21.22 |
| 24 | 3-Cl-phenyl | 2-pyridyl | $-CH_2-\underset{\underset{C_2H_5}{\|}}{\overset{}{N}}\text{(pyrrolidinyl)}$ | 117–118 | 63.9 | $C_{21}H_{25}N_6Cl$ | 63.56 63.76 | 6.30 6.55 | 21.18 20.89 |
| 25 | 4-Cl-phenyl | 2-pyridyl | $-CH_3$ | 180–181 | 96.2 | $C_{15}H_{14}N_5Cl$ | 60.10 59.85 | 4.67 4.67 | 23.40 23.40 |
| 26 | 4-Cl-phenyl | 2-pyridyl | $-C_2H_5$ | 159–160 | 98.6 | $C_{16}H_{16}N_5Cl$ | 61.24 61.04 | 5.10 5.16 | 22.33 21.98 |
| 27 | 4-Cl-phenyl | 2-pyridyl | $-CH_2CH=CH_2$ | 177 | 87.5 | $C_{17}H_{16}N_5Cl$ | 62.27 62.43 | 4.92 4.84 | 21.51 21.36 |
| 28 | 4-Cl-phenyl | 2-pyridyl | $-CH_2-\underset{\underset{C_2H_5}{\|}}{\overset{}{N}}\text{(pyrrolidinyl)}$ | 157–161 | 66.1 | $C_{21}H_{25}N_6Cl$ | 63.56 63.66 | 6.30 6.54 | 21.18 20.98 |
| 29 | 3,4-diCl-phenyl | 2-pyridyl | $-CH_3$ | 217–218 | 81.5 | $C_{15}H_{13}N_5Cl_2$ | 53.89 54.04 | 3.89 4.13 | 20.96 20.32 |
| 30 | 3,4-diCl-phenyl | 2-pyridyl | $-C_2H_5$ | 137–139 | 88.1 | $C_{16}H_{15}N_5Cl_2$ | 55.17 55.09 | 4.31 4.30 | 20.11 19.91 |
| 31 | 3,4-diCl-phenyl | 2-pyridyl | $-CH_2CH=CH_2$ | 142–144 | 70.7 | $C_{17}H_{15}N_5Cl_2$ | 56.67 56.57 | 4.17 4.12 | 19.44 19.35 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | C (Calcd/Found) | H (Calcd/Found) | N (Calcd/Found) |
|---|---|---|---|---|---|---|---|---|---|
| 32 | 3,4-dichlorophenyl | 2-pyridyl | —(CH₂)₃N(C₂H₅)₂ | 85–90 | 44.6 | C₁₇H₂₆N₆Cl₂ | 58.20 / 58.26 | 6.00 / 5.97 | 19.39 / 19.35 |
| 33 | 3,4-dichlorophenyl | 2-pyridyl | —CH₂-(1-ethylpyrrolidin-2-yl) | 130–136 | 75.5 | C₂₁H₂₄N₆Cl₂ | 58.47 / 58.65 | 5.57 / 5.62 | 19.49 / 19.36 |
| 34 | 2-methoxyphenyl | 2-pyridyl | —CH₃ | 173–174 | 78.2 | C₁₆H₁₇N₅O | 65.06 / 65.36 | 5.80 / 5.81 | 23.72 / 23.70 |
| 35 | 2-methoxyphenyl | 2-pyridyl | —C₂H₅ | 121–122 | 64.6 | C₁₇H₁₉N₅O | 66.00 / 66.17 | 6.19 / 6.34 | 22.64 / 22.63 |
| 36 | 2-methoxyphenyl | 2-pyridyl | —CH₂CH=CH₂ | 118–119 | 72.0 | C₁₈H₁₉N₅O | 67.27 / 67.21 | 5.96 / 6.02 | 21.79 / 21.74 |
| 37 | 2-methoxyphenyl | 2-pyridyl | —(CH₂)₃N(C₂H₅)₂ | 73–74 | 41.2 | C₂₂H₃₀N₆O | 66.97 / 66.91 | 7.67 / 7.84 | 21.30 / 21.22 |
| 38 | 2-methoxyphenyl | 2-pyridyl | —CH₂-(1-ethylpyrrolidin-2-yl) | 136–138 | 54.1 | C₂₂H₂₈N₆O | 67.32 / 67.56 | 7.19 / 7.43 | 21.41 / 21.20 |
| 39 | 3-methoxyphenyl | 2-pyridyl | —CH₃ | 149–150 | 71.9 | C₁₆H₁₇N₅O | 65.06 / 65.27 | 5.80 / 5.79 | 23.72 / 23.91 |
| 40 | 3-methoxyphenyl | 2-pyridyl | —C₂H₅ | 115–116 | 74.9 | C₁₇H₁₉N₅O | 66.00 / 66.22 | 6.19 / 6.17 | 22.64 / 22.87 |
| 41 | 3-methoxyphenyl | 2-pyridyl | —CH₂CH=CH₂ | 99–100 | 60.3 | C₁₈H₁₉N₅O | 67.27 / 67.72 | 5.96 / 5.85 | 21.79 / 21.94 |
| 42 | 3-methoxyphenyl | 2-pyridyl | —(CH₂)₃N(C₂H₅)₂ | 85–86 | 64.9 | C₂₂H₃₀N₆O | 66.97 / 67.04 | 7.67 / 7.74 | 21.30 / 21.38 |
| 43 | 3-methoxyphenyl | 2-pyridyl | —CH₂-(1-ethylpyrrolidin-2-yl) | 142–143 | 22.0 | C₂₂H₂₈N₆O | 67.32 / 67.40 | 7.19 / 7.14 | 21.41 / 21.54 |
| 44 | 4-methoxyphenyl | 2-pyridyl | —CH₃ | 187–188 | 74.0 | C₁₆H₁₇N₅O | 65.06 / 65.59 | 5.80 / 6.03 | 23.72 / 23.48 |

TABLE 8-continued $$\underset{B}{\overset{A}{\diagdown}} CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 45 | CH₃O—C₆H₄— | 2-pyridyl | —C₂H₅ | 144–145 | 84.9 | C₁₇H₁₉N₅O | 66.00 66.05 | 6.19 6.12 | 22.64 22.52 |
| 46 | CH₃O—C₆H₄— | 2-pyridyl | —CH₂CH=CH₂ | 139–140 | 70.0 | C₁₈H₁₉N₅O | 67.27 67.22 | 5.96 5.67 | 21.79 21.83 |
| 47 | CH₃O—C₆H₄— | 2-pyridyl | —(CH₂)₃N(C₂H₅)₂ | 74–75 | 58.6 | C₂₂H₃₀N₆O | 66.97 67.22 | 7.67 7.68 | 21.30 21.35 |
| 48 | CH₃O—C₆H₄— | 2-pyridyl | —CH₂-(N-ethylpyrrolidinyl) | 134–135 | 46.2 | C₂₂H₂₈N₆O | 67.32 67.61 | 7.19 7.15 | 21.41 21.42 |
| 49 | 3,4-(CH₃O)₂-C₆H₃— | 2-pyridyl | —CH₃ | 161–162 | 86.3 | C₁₇H₁₉N₅O₂ | 62.75 62.44 | 5.89 5.52 | 21.53 21.51 |
| 50 | 3,4-(CH₃O)₂-C₆H₃— | 2-pyridyl | —C₂H₅ | 154–155 | 80.7 | C₁₈H₂₁N₅O₂ | 63.70 63.79 | 6.24 6.20 | 20.14 20.58 |
| 51 | 3,4-(CH₃O)₂-C₆H₃— | 2-pyridyl | —CH₂CH=CH₂ | 102–103 | 64.3 | C₁₉H₂₁N₅O₂ | 64.94 65.22 | 6.02 6.12 | 19.93 19.92 |
| 52 | 3,4-(CH₃O)₂-C₆H₃— | 2-pyridyl | —(CH₂)₃N(C₂H₅)₂ | 103–104 | 49.4 | C₂₃H₃₂N₆O₂ | 65.07 65.39 | 7.60 7.64 | 19.80 20.13 |
| 53 | 3,4-(CH₃O)₂-C₆H₃— | 2-pyridyl | —CH₂-(N-ethylpyrrolidinyl) | 141–143 | 29.2 | C₂₃H₃₀N₆O₂ | 65.38 65.81 | 7.16 7.18 | 19.89 20.30 |
| 54 | 2-C₂H₅O-C₆H₄— | 2-pyridyl | —CH₃ | 149–150 | 73.8 | C₁₇H₁₉N₅O | 66.00 66.32 | 6.19 6.07 | 22.64 22.37 |
| 55 | 2-C₂H₅O-C₆H₄— | 2-pyridyl | —C₂H₅ | 139–140 | 80.7 | C₁₈H₂₁N₅O | 66.85 66.35 | 6.55 6.59 | 21.66 21.37 |
| 56 | 2-C₂H₅O-C₆H₄— | 2-pyridyl | —CH₂CH=CH₂ | 112–113 | 73.9 | C₁₉H₂₁N₅O | 68.04 68.34 | 6.31 6.16 | 20.88 20.35 |
| 57 | 2-C₂H₅O-C₆H₄— | 2-pyridyl | —(CH₂)₃N(C₂H₅)₂ | 84–85 | 59.0 | C₂₃H₃₂N₆O | 67.62 68.00 | 7.90 8.09 | 20.57 20.72 |

TABLE 8-continued $$\begin{array}{c} A \\ \diagdown \\ CHNH-C-NHR \\ \diagup \\ B \end{array} \quad \begin{array}{c} NCN \\ \| \end{array}$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 58 | 2-OC$_2$H$_5$-C$_6$H$_4$ | 2-pyridyl | —CH$_2$-(1-ethylpyrrolidin-2-yl) | 121–123 | 70.6 | C$_{23}$H$_{30}$N$_6$O | 67.85 68.34 | 7.44 7.48 | 20.67 20.80 |
| 59 | 2-iso-OC$_3$H$_7$-C$_6$H$_4$ | 2-pyridyl | —CH$_3$ | 148–149 | 69.5 | C$_{18}$H$_{21}$N$_5$O | 66.85 67.25 | 6.55 6.52 | 21.66 21.88 |
| 60 | 2-iso-OC$_3$H$_7$-C$_6$H$_4$ | 2-pyridyl | —C$_2$H$_5$ | 141–142 | 72.6 | C$_{19}$H$_{23}$N$_5$O | 67.63 67.55 | 6.87 6.75 | 20.76 20.39 |
| 61 | 2-iso-OC$_3$H$_7$-C$_6$H$_4$ | 2-pyridyl | —CH$_2$CH=CH$_2$ | 120–121 | 62.4 | C$_{20}$H$_{23}$N$_5$O | 68.74 68.59 | 6.63 6.56 | 20.04 20.00 |
| 62 | 2-iso-OC$_3$H$_7$-C$_6$H$_4$ | 2-pyridyl | —(CH$_2$)$_3$N(C$_2$H$_5$)$_2$ | 100–101 | 83.7 | C$_{24}$H$_{34}$N$_6$O | 68.21 68.33 | 8.11 8.35 | 19.89 20.10 |
| 63 | 2-iso-OC$_3$H$_7$-C$_6$H$_4$ | 2-pyridyl | —CH$_2$-(1-ethylpyrrolidin-2-yl) | 134–136 | 45.3 | C$_{24}$H$_{32}$N$_6$O | 68.54 69.15 | 7.67 7.76 | 19.99 20.49 |
| 64 | 4-CH$_3$S-C$_6$H$_4$ | 2-pyridyl | —CH$_3$ | 206–207 | 65.4 | C$_{16}$H$_{17}$N$_5$S | 61.72 62.01 | 5.50 5.39 | 22.50 22.52 |
| 65 | 4-CH$_3$S-C$_6$H$_4$ | 2-pyridyl | —C$_2$H$_5$ | 132–133 | 66.6 | C$_{17}$H$_{19}$N$_5$S | 62.75 62.55 | 5.89 5.66 | 21.53 21.38 |
| 66 | 4-CH$_3$S-C$_6$H$_4$ | 2-pyridyl | —CH$_2$CH=CH$_2$ | 111–112 | 68.1 | C$_{18}$H$_{19}$N$_5$S | 64.08 64.28 | 5.68 5.59 | 20.76 20.66 |
| 67 | 4-CH$_3$S-C$_6$H$_4$ | 2-pyridyl | —(CH$_2$)$_3$N(C$_2$H$_5$)$_2$ | 88–89 | 52.8 | C$_{22}$H$_{30}$N$_6$S | 64.36 64.68 | 7.37 7.61 | 20.47 20.26 |
| 68 | 4-CH$_3$S-C$_6$H$_4$ | 2-pyridyl | —CH$_2$-(1-ethylpyrrolidin-2-yl) | 132–133 | 64.3 | C$_{22}$H$_{28}$N$_6$S | 64.68 64.81 | 6.91 6.82 | 20.58 20.55 |
| 69 | 4-CH$_3$SO$_2$-C$_6$H$_4$ | 2-pyridyl | —CH$_3$ | 152–153 | 67.2 | C$_{16}$H$_{17}$N$_5$O$_2$S | 55.97 55.76 | 4.99 4.74 | 20.40 20.27 |
| 70 | 4-CH$_3$SO$_2$-C$_6$H$_4$ | 2-pyridyl | —C$_2$H$_5$ | 109–110 | 62.5 | C$_{17}$H$_{19}$N$_5$O$_2$S | 57.13 57.18 | 5.36 5.65 | 19.60 19.68 |
| 71 | 4-CH$_3$SO$_2$-C$_6$H$_4$ | 2-pyridyl | —CH$_2$CH=CH$_2$ | 124–125 | 64.5 | C$_{18}$H$_{19}$N$_5$O$_2$S | 58.53 58.75 | 5.19 5.08 | 18.96 18.97 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found ||| 
|---|---|---|---|---|---|---|---|---|---|
| | | | | | | | C | H | N |
| 72 | CH₃SO₂—C₆H₄— | 2-pyridyl | —(CH₂)₃N(C₂H₅)₂ | 127–129 | 28.2 | $C_{22}H_{30}N_6O_2S$ | 57.37 / 57.36 | 7.00 / 7.11 | 18.25 / 18.05 |
| 73 | CH₃SO₂—C₆H₄— | 2-pyridyl | —CH₂-(N-ethylpyrrolidin-2-yl) | 155–156 | 29.2 | $C_{22}H_{28}N_6O_2S$ | 59.98 / 60.17 | 6.41 / 6.53 | 19.08 / 18.69 |
| 74 | 3-CF₃-C₆H₄— | 2-pyridyl | —CH₃ | 175–176 | 63.0 | $C_{16}H_{14}N_5F_3$ | 57.65 / 57.54 | 4.23 / 4.25 | 21.01 / 21.00 |
| 75 | 3-CF₃-C₆H₄— | 2-pyridyl | —C₂H₅ | 158–159 | 70.7 | $C_{17}H_{16}N_5F_3$ | 58.78 / 58.58 | 4.64 / 4.64 | 20.16 / 20.20 |
| 76 | 3-CF₃-C₆H₄— | 2-pyridyl | —CH₂CH=CH₂ | 115–116 | 64.3 | $C_{18}H_{16}N_5F_3$ | 60.16 / 60.07 | 4.49 / 4.50 | 19.49 / 19.53 |
| 77 | 3-CF₃-C₆H₄— | 2-pyridyl | —(CH₂)₃N(C₂H₅)₂ | 74–75 | 39.6 | $C_{22}H_{27}N_6F_3$ | 61.09 / 61.28 | 6.29 / 6.08 | 19.43 / 19.56 |
| 78 | 3-CF₃-C₆H₄— | 2-pyridyl | —CH₂-(N-ethylpyrrolidin-2-yl) | 137–138 | 60.6 | $C_{22}H_{25}N_6F_3$ | 61.38 / 61.36 | 5.84 / 5.87 | 19.52 / 19.60 |
| 79 | C₆H₅— | 2-pyridyl N-oxide | —CH₃ | 178–181 | 84.9 | $C_{15}H_{15}N_5O$ | 64.06 / 63.80 | 5.34 / 5.08 | 24.91 / 24.77 |
| 80 | C₆H₅— | 2-pyridyl N-oxide | —C₂H₅ | 97–98 | 58.6 | $C_{16}H_{17}N_5O$ | 65.08 / 64.92 | 5.76 / 5.60 | 23.73 / 23.49 |
| 81 | C₆H₅— | 2-pyridyl N-oxide | —CH₂CH=CH₂ | 167–168 | 67.9 | $C_{17}H_{17}N_5O$ | 66.45 / 66.80 | 5.54 / 5.38 | 22.80 / 22.76 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|-----|---|---|---|---|---|---|---|---|---|
| | | | | | | | C | H | N |
| 82 | phenyl | 2-pyridyl N-oxide | $-(CH_2)_3N(C_2H_5)_2$ | 128–129 | 70.6 | $C_{21}H_{28}N_6O$ | 66.32 66.35 | 7.37 7.44 | 22.11 22.01 |
| 83 | phenyl | 2-pyridyl N-oxide | $-CH_2-$(1-ethylpyrrolidin-2-yl) | 185–187 | 34.9 | $C_{21}H_{26}N_6O$ | 66.64 66.31 | 6.92 6.93 | 22.21 21.91 |
| 84 | 2-furyl | 2-pyridyl | $-CH_3$ | 141–143 | 72.8 | $C_{13}H_{12}N_5O$ | 61.40 61.49 | 4.75 5.03 | 27.54 27.76 |
| 85 | 2-furyl | 2-pyridyl | $-C_2H_5$ | 131–133 | 72.6 | $C_{14}H_{15}N_5O$ | 62.43 62.74 | 5.61 5.66 | 26.00 26.30 |
| 86 | 2-furyl | 2-pyridyl | $-CH_2CH=CH_2$ | 129–130 | 87.0 | $C_{15}H_{15}N_5O$ | 64.03 64.30 | 5.37 5.66 | 24.90 25.35 |
| 87 | 2-thienyl | 2-pyridyl | $-CH_3$ | 137–139 | 66.0 | $C_{13}H_{13}N_5S$ | 57.53 57.87 | 4.82 4.85 | 25.81 25.77 |
| 88 | 2-thienyl | 2-pyridyl | $-C_2H_5$ | 161–163 | 64.9 | $C_{14}H_{15}N_5S$ | 58.91 58.95 | 5.29 5.16 | 24.54 24.26 |
| 89 | 2-thienyl | 2-pyridyl | $-CH_2CH=CH_2$ | 123–125 | 73.9 | $C_{15}H_{15}N_5S$ | 60.57 60.90 | 5.08 4.97 | 23.55 23.24 |
| 90 | 2-thienyl | 2-pyridyl | $-CH_2-$(1-ethylpyrrolidin-2-yl) | 112–114 | 53.1 | $C_{19}H_{24}N_6S$ | 61.92 61.91 | 6.56 6.23 | 22.81 22.61 |
| 91 | cyclohexyl | 2-pyridyl | $-CH_3$ | 195–197 | 76.1 | $C_{15}H_{21}N_5$ | 66.38 66.23 | 7.80 7.90 | 25.81 25.74 |
| 92 | cyclohexyl | 2-pyridyl | $-C_2H_5$ | 153–155 | 78.5 | $C_{16}H_{23}N_5$ | 67.33 67.48 | 8.12 8.18 | 24.54 24.56 |
| 93 | cyclohexyl | 2-pyridyl | $-CH_2CH=CH_2$ | 100–102 | 53.6 | $C_{17}H_{23}N_5$ | 68.65 68.89 | 7.79 8.07 | 23.55 23.72 |

TABLE 8-continued $$\underset{B}{\overset{A}{>}}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 94 |  | 2-pyridyl | 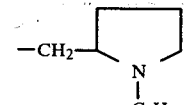 | 148–151 | 41.9 | $C_{21}H_{32}N_6$ | 68.43 / 68.28 | 8.75 / 8.90 | 22.80 / 22.65 |
| 95 |  |  | —CH₃ | 147–150 | 78.5 | $C_{16}H_{16}N_4$ | 72.70 / 73.01 | 6.10 / 6.05 | 21.20 / 21.06 |
| 96 |  |  | —C₂H₅ | 145–146 | 82.2 | $C_{17}H_{18}N_4$ | 73.34 / 73.47 | 6.53 / 6.73 | 20.13 / 20.13 |
| 97 |  |  | —CH₂CH=CH₂ | 149–150 | 78.8 | $C_{18}H_{18}N_4$ | 74.45 / 74.78 | 6.25 / 6.11 | 19.30 / 19.20 |
| 98 |  |  | —(CH₂)₃N(C₂H₅)₂ | 122–124 | 82.6 | $C_{22}H_{29}N_5$ | 72.69 / 73.21 | 8.04 / 7.95 | 19.27 / 19.22 |
| 99 | 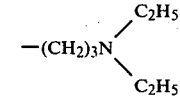 |  |  | 176–178 | 71.2 | $C_{22}H_{27}N_5$ | 73.09 / 73.29 | 7.53 / 7.49 | 19.38 / 19.24 |
| 100 | 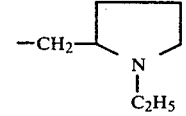 | 2-pyridyl | —CH₃ | 192–193 | 71.7 | $C_{17}H_{19}N_5O$ | 66.00 / 66.30 | 6.19 / 6.11 | 22.64 / 22.56 |
| 101 | 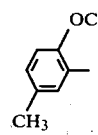 | 2-pyridyl | —C₂H₅ | 136–137 | 79.8 | $C_{18}H_{21}N_5O$ | 66.85 / 67.12 | 6.55 / 6.53 | 21.66 / 21.72 |
| 102 | 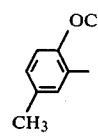 | 2-pyridyl | —CH₂CH=CH₂ | 131–132 | 71.3 | $C_{19}H_{21}N_5O$ | 68.04 / 68.21 | 6.31 / 6.25 | 20.88 / 20.62 |
| 103 | 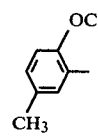 | 2-pyridyl | —n-C₃H₇ | 119–120 | 87.3 | $C_{18}H_{21}N_5O$ | 66.85 / 67.30 | 6.55 / 6.63 | 21.66 / 21.64 |
| 104 | 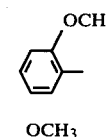 | 2-pyridyl | —(CH₂)₂N(C₂H₅)₂ | 105–106 | 46.6 | $C_{21}H_{28}N_6O$ | 66.29 / 66.60 | 7.42 / 7.55 | 22.99 / 22.39 |
| 105 | 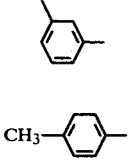 | 2-pyridyl | —(CH₂)₃N(CH₃)₂ | 122–123 | 74.4 | $C_{20}H_{26}N_6$ | 68.54 / 68.95 | 7.48 / 7.47 | 23.98 / 23.89 |
| 106 | 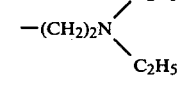 | 2-pyridyl | —n-C₄H₉ | 175–176 | 89.0 | $C_{18}H_{20}N_5Cl$ | 63.25 / 63.40 | 5.86 / 5.98 | 20.50 / 20.45 |

TABLE 8-continued $$A\diagdown_{B\diagup}CHNH-\overset{NCN}{\underset{\|}{C}}-NHR$$

| Ex. | A | B | R | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 107 | 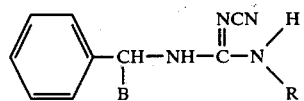 OC₂H₅ | 2-pyridyl | —CH₂CH(CH₃)(CH₃) | 92–95 | 84.2 | C₂₀H₂₅N₅O | 68.34 68.41 | 7.18 7.17 | 19.93 19.86 |

EXAMPLE 108

Five grams (0.018 mol) of N-cyano-N'-[α-(2-pyridyl)-benzyl]-S-methylisothiourea and 5 g (0.057 mol) of N,N-dimethylethylenediamine were dissolved in 100 ml of ethanol, and the whole was reacted under reflux for 10–15 hours. The reaction solution was concentrated under a reduced pressure. The residue was washed with water, followed by recrystalizing from ethyl acetate to produce 3.4 g of N-cyano-N'-(2-dimethylamino)ethyl-N-[α-(2-pyridyl)benzyl]guanidine (yield: 58.7%).

Melting point: 142°–4° C.

Elementary analysis (%) for C₁₈H₂₂N₆:

| | C | H | N |
|---|---|---|---|
| Calculated: | 67.04 | 6.89 | 26.07 |
| Found: | 67.09 | 6.97 | 25.96 |

EXAMPLES 109–123

The following Table 9 shows the compounds which were prepared using the procedures similar to Example 108.

In Table 9 Part I, the general formula:

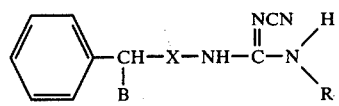

represents the formula wherein A is phenyl, B is pyridyl, and p is 0 in the formula (I) hereinbefore mentioned.

In Table 9 Part II, the general formula:

$$\text{Ph}-\underset{B}{\underset{|}{CH}}-X-NH-\overset{NCN}{\underset{\|}{C}}-N\diagup^{H}\diagdown_{R}$$

represents the formula wherein A is phenyl, B is pyridyl, and p is 1 in the formula (I).

TABLE 9

| Ex. | B | R | X | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| | | $\text{Ph}-\underset{B}{\underset{|}{CH}}-NH-\overset{NCN}{\underset{\|}{C}}-N\diagup^{H}\diagdown_{R}$ | | | | | | | |
| 109 | 2-pyridyl | —(CH₂)₂N(C₂H₅)(C₂H₅) | | 151–152 | 82.5 | C₂₀H₂₆N₆ | 68.53 68.76 | 7.49 7.56 | 23.98 23.97 |
| 110 | 2-pyridyl | —(CH₂)₃N(CH₃)(CH₃) | | 143 | 86.0 | C₁₉H₂₄N₆ | 67.83 67.87 | 7.19 7.47 | 24.98 24.11 |
| 111 | 2-pyridyl | —(CH₂)₃N(C₂H₅)(C₂H₅) | | 84–85 | 58.0 | C₂₁H₂₈N₆ | 69.18 69.21 | 7.76 7.81 | 23.06 22.89 |

TABLE 9-continued

| Ex. | B | R | X | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 112 | 2-pyridyl | $-CH_2-\underset{\underset{C_2H_5}{|}}{N}$ (pyrrolidinyl) | | 136–137 | 67.5 | $C_{21}H_{26}N_6$ | 69.58 70.15 | 7.23 7.44 | 23.19 23.17 |
| 113 | 2-pyridyl | $-(CH_2)_3-N\underset{}{\bigcirc}O$ (morpholino) | | 142–143 | 75.8 | $C_{21}H_{26}N_6O$ | 66.64 67.07 | 6.92 6.97 | 22.21 22.72 |
| 114 | 3-pyridyl | $-(CH_2)_3N(C_2H_5)_2$ | | 97–98 | 64.8 | $C_{21}H_{28}N_6$ | 69.19 69.24 | 7.74 7.70 | 23.06 23.12 |
| 115 | 3-pyridyl | $-CH_2-\underset{\underset{C_2H_5}{|}}{N}$ (pyrrolidinyl) | | 148–150 | 53.1 | $C_{21}H_{21}N_6$ | 69.58 69.36 | 7.23 7.22 | 23.19 23.51 |
| 116 | 4-pyridyl | $-(CH_2)_3N(C_2H_5)_2$ | | 133–135 | 51.1 | $C_{21}H_{28}N_6$ | 69.19 69.12 | 7.74 7.87 | 23.06 23.01 |
| 117 | 4-pyridyl | $-CH_2-\underset{\underset{C_2H_5}{|}}{N}$ (pyrrolidinyl) | | 166–168 | 44.05 | $C_{21}H_{21}N_6$ | 69.58 69.80 | 7.23 7.12 | 23.19 23.24 |
| 118 | 2-pyridyl | $-(CH_2)_2-N\bigcirc$ (piperidino) | | 155–158 | 73.0 | $C_{20}H_{24}N_6$ | 68.92 69.36 | 6.96 7.02 | 24.12 24.12 |
| 119 | 2-pyridyl | $-(CH_2)_3-N$(2-methylpiperidyl) | | 99–101 | 72.6 | $C_{23}H_{30}N_6$ | 70.72 70.87 | 7.76 7.58 | 21.52 21.11 |

$$\text{C}_6\text{H}_5\text{-CH(B)-X-NH-}\underset{\underset{R}{|}}{\overset{\overset{NCN}{||}}{C}}\text{-N(H)R}$$

| Ex. | B | R | X | Melting Point (°C.) | Yield | Molecular Formula | C | H | N |
|---|---|---|---|---|---|---|---|---|---|
| 120 | 2-pyridyl | $-(CH_2)_3N(C_2H_5)_2$ | $-CH_2-$ | 104–105 | 41.0 | $C_{22}H_{30}N_6$ | 69.81 69.75 | 7.99 7.90 | 22.20 22.08 |
| 121 | 2-pyridyl | $-CH_2-\underset{\underset{C_2H_5}{|}}{N}$ (pyrrolidinyl) | $-CH_2-$ | 136–138 | 40.8 | $C_{22}H_{23}N_6$ | 70.18 70.38 | 7.50 7.63 | 22.32 22.46 |
| 122 | 2-pyridyl | $-(CH_2)_3N(C_2H_5)_2$ | $-(CH_2)_2S-$ | 94–95 | 47.1 | $C_{23}H_{32}N_6S$ | 65.06 65.23 | 7.60 7.54 | 19.79 19.85 |

TABLE 9-continued

| Ex. | B | R | X | Melting Point (°C.) | Yield | Molecular Formula | Elementary Analysis Upper line: Calcd. Lower line: Found | | |
|---|---|---|---|---|---|---|---|---|---|
| | | | | | | | C | H | N |
| 123 | 2-pyridyl | 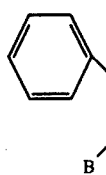 | —(CH$_2$)$_2$S— | 130–131 | 41.9 | C$_{23}$H$_{30}$N$_6$S | 65.37<br>65.48 | 7.16<br>7.36 | 19.89<br>19.11 |

What is claimed is:

1. A compound of the formula

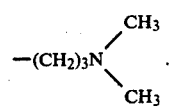

wherein B is 2-, 3- or 4-pyridyl, R represents a group of the formula:

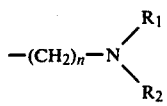

wherein R$_1$ and R$_2$ are the same or different, and each represent a lower alkyl group, or together form a nitrogen-containing heterocycle of 5-member ring or 6-member ring which ring may also contain oxygen as hetero atom, and n is an integer of 1–3, or R represents a group of the formula

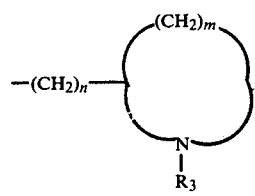

wherein R$_3$ is a lower alkyl group, n is an integer of 1–3, and m is an integer of 4–5.

2. A compound according to claim 1 wherein B is 2-pyridyl and R is

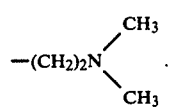

3. A compound according to claim 1 wherein B is 2-pyridyl and R is

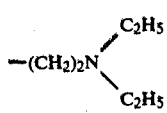

4. A compound according to claim 1 wherein B is 2-pyridyl and R is

—(CH$_2$)$_3$N(CH$_3$)$_2$

5. A compound according to claim 1 wherein B is 2-pyridyl and R is

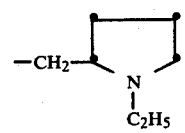

6. A compound according to claim 1 wherein B is 2-pyridyl and R is

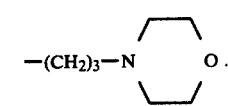

7. A compound according to claim 1 wherein B is 2-pyridyl and R is

—(CH$_2$)$_3$—N⌇O .

8. A compound according to claim 1 wherein B is 3-pyridyl and R is

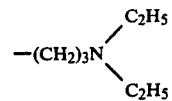

9. A compound according to claim 1 wherein B is 3-pyridyl and R is

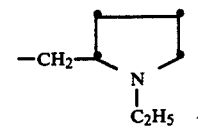

10. A compound according to claim 1 wherein B is 4-pyridyl and R is

−(CH₂)₃N(C₂H₅)(C₂H₅) 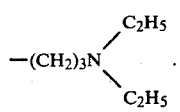
11. A compound according to claim 1 wherein B is 4-pyridyl and R is
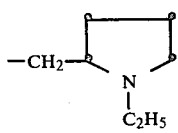
12. A compound according to claim 1 wherein B is 2-pyridyl and R is
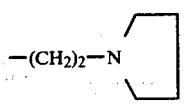
13. A compound according to claim 1 wherein B is 2-pyridyl and R is
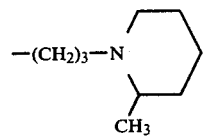
* * * * *